(12) United States Patent
Tazawa

(10) Patent No.: US 7,361,759 B2
(45) Date of Patent: Apr. 22, 2008

(54) METHOD FOR PRODUCING L-BIOPTERIN

(75) Inventor: Shinnosuke Tazawa, Chiba (JP)

(73) Assignees: Shiratori Pharmaceutical Co., Ltd, Narashino-shi (JP); Asubio Pharma Co., Ltd., Tokyo (JP)

( * ) Notice: Subject to any disclaimer, the term of this patent is extended or adjusted under 35 U.S.C. 154(b) by 55 days.

(21) Appl. No.: 11/066,255

(22) Filed: Feb. 28, 2005

(65) Prior Publication Data
US 2006/0142573 A1  Jun. 29, 2006

(30) Foreign Application Priority Data
Dec. 27, 2004  (JP)  ............................. 2004-375618

(51) Int. Cl.
*C07D 475/04* (2006.01)
*C07H 19/19* (2006.01)
(52) U.S. Cl. ..................................... 544/259; 536/27.4
(58) Field of Classification Search ................. 544/259
See application file for complete search history.

(56) References Cited

FOREIGN PATENT DOCUMENTS

| CH | 500 999 | 12/1970 |
|---|---|---|
| EP | 0 165 595 | 12/1985 |
| EP | 0 385 336 | 9/1990 |
| JP | 58-83691 | 5/1983 |
| JP | 59-112987 | 6/1984 |
| JP | 59-186986 | * 10/1984 |
| JP | 2-31720 | 7/1990 |
| JP | 2-55434 | 11/1990 |
| JP | 3-32553 | 5/1991 |
| JP | 2567637 | 10/1996 |
| JP | 2567638 | 10/1996 |
| JP | 2567639 | 10/1996 |
| JP | 2575781 | 11/1996 |
| JP | 2611790 | 2/1997 |
| JP | 2674707 | 7/1997 |
| JP | 2843592 | 10/1998 |
| JP | 2001-302665 | 10/2001 |

OTHER PUBLICATIONS

Wikipedia, definition of "derivative," Feb. 2007.*
Wikipedia, "Lithium chloride." http:en.eikipedia.org/wiki/Lithium_chloride, last modified, Nov. 19, 2007.*
Bernhard Schircks, et al., "169. Pterinechemistry Part 84[1]) A New, Regiospecific Synthesis of L-Biopterin[2]", Helvetica Chimica Acta, Pterinechemistry, vol. 68, No. 6, 1985, pp. 1639-1643.
Anne-Marie Fernandez, et al., "Total Synthesis of L-Biopterin from L-Tartaric Acid via 5-Deoxy-L-arabinose", J. Org Chem., vol. 61, No. 24, 1996, pp. 8698-8700.
Anne-Marie Fernandez, et al., "Optically Pure Dihydroxy γ-Alkylated γ-Butyrolactones Starting from L-Tartaric Acid: Application to Formal and Total Syntheses of Natural Products", J. Org. Chem., vol. 62, No. 12, 1997, pp. 4700-4014.
Tadashi Hanaya, et al., "Pteridines CV. Selective N(3)-and O[4]-Alkylation of L-Biopterin : A Convenient Synthesis of 3-and O[4]-Methyl-L-biopterin and the Versatile N[2]-(N,N-dimethylaminomethylene)-N(3)-p-nitrophenethyl-Protected L-Biopterin", Pteridines, vol. 6, No. 1, 1995, pp. 1-7.
Shizuaki Murata, et al., Novel Regio-and Stereoselective Synthesis of 6-Substituted Pteridines and Naturally Occurring L-erythro-Biopterin, Synthesis, Mar. 1992, pp. 303-308.
Kenji Mori, et al., "A New Synthesis of (−)-Biopterin Employing 5-Deoxy-L-ribose as a Key Intermediate", Liebigs Ann. Chem. 1989, pp. 1267-1269.
Haruhiko Kikuchi, et al., "Synthesis of (−)-Biopterin Using (S)-Ethyl Lactate as a Starting Material", Agric. Biol. Chem., vol. 53, No. 8, 1989, pp. 2095-2100.
Kenji Mori, et al., "Synthesis of (−)-Biopterin", Liebigs Ann. Chem., 1989, pp. 963-967.

(Continued)

*Primary Examiner*—Mark L Berch
*Assistant Examiner*—Cecilia Jaisle
(74) *Attorney, Agent, or Firm*—Oblon, Spivak, McClelland, Maier & Neustadt, P.C.

(57) ABSTRACT

To provide a method for producing L-biopterin on a large industrial scale by using a reagent which is inexpensive and easy to handle, without requiring a use of any particular equipment or plants.

A method for porducing a biopterin derivative represented by the formula (6):

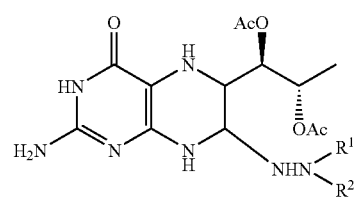

(6)

wherein $R^1$ and $R^2$, which are the same or different from each other, each represents a hydrogen atom, an alkyl group, or an aryl group, comprising:
reacting a compound belonging to triacetoxy-5-deoxy-L-arabinose phenylhydrazones represented by the formula (4):

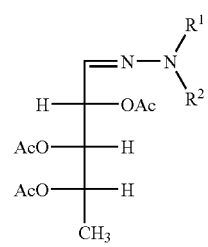

(4)

wherein $R^1$ and $R^2$ are the same as defined above,
with 6-hydroxy-2,4,5-triaminopyrimidine (5) under catalytic influence of a Lewis acid in an aqueous solvent.

14 Claims, No Drawings

OTHER PUBLICATIONS

Ado Kaiser, et al., "80. Synthesis of Biopterin from Neopterin? The Formation of Pyrrolo [1,2-*f*] pteridins upon Side-Chain Activation of Neopterin", Helvetica Chimica Acta., vol. 70, No. 3, 1987, pp. 766-770.

Mathias Kappel, et al.,"Synthese und Eigenschaften von Biopterin und Biopterin-Analogen", Liebigs Ann., Chem., 1984, pp. 1815-1825 (with English summery).

Wilfred L. F. Armarego, et al., "Pterins. VIII. The Absolute Configuration at C 6 of Natural 2-Amino-6-[1'R,2'S]-1',2'-dihydroxypropyl-5,6,7,8-tetrahydropteridin-4(3H)-one (L-erythro-5,6,7,8-Tetrahydrobiopterin)", Aust. J. Chem., vol. 35, No. 4, 1982, pp. 785-793.

Takashi Sugimoto, et al., "Studies on Biologically Active Pteridines. IV.[1)] Synthesis of Several Biopterin Derivatives as an Antigen in Radioimmunoassay for Biopterin", Bull. Chem., Soc. Jpn., vol. 53, No. 8, 1980, pp. 2344-2347.

Shoji Watabe, "Purification and Characterization of Tetrahydrofolate. Protein Complex in Bovine Liver", The Journal of Biological Chemistry, vol. 253, No. 19, Oct. 10, 1978, pp. 6673-6679.

"Synthesis of biopterin without the by-production of isobiopterin", Bitamin, vol. 51, No. 12, 1977, pp. 544-545 (with partial English translation).

Bernhard Schircks, et al., "Eine neue, regiospezifische Synthese von L-Biopterin", 24. Über Pterinchemie, Helvetica Chimica Acta, vol. 60, Fasc.1, Nr. 24, 1977, pp. 211-215 (with English summery).

Edward C. Taylor, et al., "Pteridines. XXXVII. A Total Synthesis of L-erythro-Biopterin and Some Related 6-(Polyhydroxyalkyl) pterins", Journal of the American Chemical Society, vol. 98, No. 8, 1976, pp. 2301-2307.

Takashi Sugimoto, et al., "The Convenient Syntheses of Biopterin and Its Three Opitical Isomers", Bulletin of the Chemical Society of Japan, vol. 48, No. 12, 1975, pp. 3767-3768.

"Pteridines. XXXIII. Unequivocal total synthesis of L-erythro-biopterin", Journal of the American Chemical Society, vol. 96, No. 21, 1974, pp. 6781-6782.

M. Viscontini, et al., "Weiterer Beitrag zur Synthese des Biopterins", 60. Über Pterinchemie, Helvetica Chimica Acta, vol. 55, Fasc. 2, Nr. 60, 1972, pp. 570-574 (with partial English translation).

K. J. M. Andrews, et al., "A New Synthesis of Biopterin", Journal of the Chemical Society Sec. C., No. 6, 1969, pp. 928-930.

Ki W. Cha, et al., "46. Pteridines Part CVI[1)] Isolation and Characterization of Limipterin (1-O-(L-erythro-Biopterin-2'-yl)-β-N-acetylglucosamine) and Its 5,6,7,8-Tetrahydro Derivative from Green Sulfur Bacterium Chlorobium limicola f. thiosulfatophilum NCIB 8327", Helvetica Chimica Acta, vol., 78, 1995, pp. 600-614.

H. S. Forrest, et al., "Pteridines from Drosophila. III. Isolation and Identification of Three More Pteridines", Journal of the American Chemical Society, vol. 77, Sep. 20, 1955, pp. 4865-4869.

E. L. Patterson, et al., "The Synthesis of a Pteridine Required for the Growth of Crithidia Fasciculata", Journal of the American Chemical Society, vol. 78, 1956, pp. 5868-5871.

M. Viscontini, et al., "Synthese und Eigenschaften des L-erythro-2-Amino-6-hydroxy-8-dihydroxypropyl-pteridins und des D-threo-2-Amino-6-hydroxy-8-dihydroxypropyl-pteridins", Helvetica Chimica Acta, vol. 41, 1958, pp. 108-113 (with partial English translation).

Adolf Butenandt, et al., "Isolierung von 2-Amino-4-hydroxy-6-[1,2-dihydroxy-propyl]-pteridin", Hoppe-Seyler's Z. Physiol. Chem., Bd. 311, 1958, pp. 79-83 (with English summery).

Max Viscontini, "The Synthesis of L-Biopterin", Biochemical and Clinical Aspects of Pteridines, vol. 3, 1984, pp. 19-33.

* cited by examiner

METHOD FOR PRODUCING L-BIOPTERIN

FIELD OF THE INVENTION

The present invention relates to a method for producing L-biopterin on an industrial scale.

BACKGROUND OF THE INVENTION

L-biopterin is known in the art as a raw material for the preparation of sapropterin hydrochloride (hydrochloride salt of L-tetrahydrobiopterin). Sapropterin hydrochloride is a drug used for the treatment of atypical hyperphenylalaninemia. Although sapropterin hydrochloride is typically prepared by reducing L-biopterin, there is a growing need for the development of an improved method for the preparing of this starting material, namely L-biopterin, in a manner suited to its large scale production.

Heretofore, it is known to prepare L-biopterin using 1',1'-diethylsulfonyl-L-rhamnose (REM oxide) as its starting material and going through a phenylhydrazone compound as its intermediate product. (See nonpatent literature 1.)

Methods known in the prior art for synthesizing this phenylhydrazone compound as an synthetic intermediate of L-biopterin include obtaining the phenylhydrazone compound from L-rhamnose as a starting material via L-rhamnose diethyl mercaptal (REM) and then 5-deoxy-L-arabinose (5-DA) as intermediate products (See patent literature 1 and nonpatent literature 2.), obtaining the phenylhydrazone compound from L-arabinose through 5-DA (See patent literature 2.), obtaining the phenylhydrazone compound from tartaric acid (See nonpatent literatures 3 and 4.), and obtaining the phenylhydrazone compound from R-ribose (See patent literature 3.).

However, the prior art method of preparing the phenylhydrazone compound ribose from tartaric acid or R-ribose is not adequate for industrial scale production in that such a method involves a longer process and a lower yield and that a low-temperature step or silica gel refining step is involved in the process. Meanwhile, the above-described other method preparing the phenylhydrazone compound from L-rhamnose directly or from L-rhamnose through 5-DA requires such processes that are disadvantageous from a viewpoint of industrial scale production, including water concentrating and resin refining by desalination for 5-DA isolation, and reaction solution concentrating using RO (reverse osmosis) or like equipment.

The resultant phenylhydrazone compound is reacted with an acetylating agent in pyridine to obtain a triacetylated compound, which is then condensed and cyclized with 6-hydroxy-2,4,5-triaminopyrimidine (TAU) in the coexistence of sodium acetate to obtain a biopterin derivative. After oxidized with iodine or other oxidizing agent, the biopterin derivative is subjected to deacetylation (hydrolysis) to produce L-biopterin.

However, the acetylation process used in the prior art described above requires a use of an excessive quantity of pyridine with an enormous increase in quantity of the reaction solution used in the subsequent processes, resulting in decreased productivity. Also, the above-described cyclization provided substantially as a continuation of its preceding process inevitably involves a use of an enormous quantity of the reaction solution, while decreasing its reaction solvent causes a remarkable reduction in yield due to solubility of the TAU. Further, the prior art method just described is not adequate for a large scale industrial production of L-biopterin, because iodine used as an oxidizing agent in its oxidation process is not only costly, but also has sublimatability and toxicity possibly giving rise to problems in respect of working health and wastewater treatment.

[Patent literature 1] Japanese published unexamined patent application JP A S59-186986
[Patent literature 2] European published unexamined patent application EP 0165595
[Patent literature 3] European published unexamined patent application EP 0385338
[Nonpatent literature 1] Helv. Chim. Acta 68(6) 1639-43 (1985)
[Nonpatent literature 2] J. Org. Chem. 1996, 61,.8698-8700
[Nonpatent literature 3] J. Org. Chem. 1997, 62, 4007-4014

DISCLOSURE OF THE INVENTION

[Problems to be Solved by the Invention]

An object of the present invention is to provide a method for producing L-biopterin in a manner adapted for its large scale industrial production by using a reagent which is inexpensive and easy to handle, without requiring a use of any particular equipment or plants. Also, the present invention provides such a method for producing L-biopterin adapted for its large scale industrial production that allows a reaction solution to decrease to improve the productivity.

[Means to Solve the Problems]

As a result of a series of researches made in an effort to provide a method for producing L-biopterin in volume in good yield, the inventors have found that turning 5-DA into a hydrazone compound in an aqueous solvent and distributing it in an organic solvent separating from water allows the method to dispense with the 5-DA isolation and thereby to do away with any industrially disadvantageous processes such as a water concentrating process. Further, the inventors have found that reacting an acetylating agent with the hydrazone compound as dissolved in this organic solvent allows it to be acetylated only with a catalytic quantity of a dialkylaminopyridine. Furthermore, it has been found that in cyrclization process the yield can be improved and the volume of a reactant solvent used can be decreased by subjecting the hydrazone compound to condensation with TAU under the catalytic influence of a Lewis acid. In addition, it has been found that the oxidation process may employ inexpensive hydrogen peroxide for effecting its oxidative reaction, and the present invention has been accomplished based on these finding by the inventors.

Specifically, the present invention provides a method for producing a biopterin derivative represented by the formula (6):

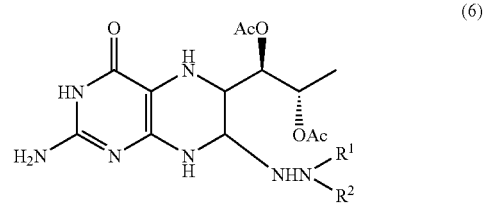

(6)

wherein $R^1$ and $R^2$, which are the same or different from each other, each represents an hydrogen atom, an alkyl group, or aryl group, comprising:
reacting a compound belonging to triacetoxy-5-deoxy-L-arabinose hydrazones represented by the formula (4):

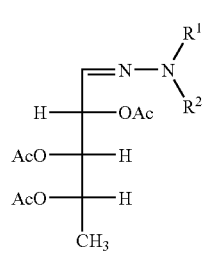

(4)

wherein R¹ and R² are the same as defined above, with 6-hydroxy-2,4,5-triaminopyrimidine (5) under the catalytic influence of a Lewis acid in an aqueous solvent.

Also, the present invention provides a method for producing 1',2'-O-diacetyl-L-biopterin, comprising oxidizing the biopterin derivative represented by the foregoing formula (6) obtainable by the method described just above.

Further, the present invention provides a method for producing L-biopterin, comprising hydrolyzing the 1',2'-O-diacetyl-L-biopterin obtainable by the method described above.

Furthermore, the present invention provides a method for producing the compound represented by the foregoing formula (4), comprising:

reacting a compound represented by the formula (3):

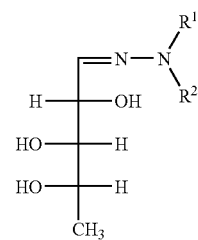

(3)

wherein R¹ and R² are the same as defined above, with an acetylating agent in the presence of a catalytic quantity of a dialkylaminopyridine.

Yet further, the present invention provides a method for producing the compound represented by the foregoing formula (4), wherein the compound represented by the foregoing formula (3) is obtainable by reacting 5-deoxy-L-arabinose with a hydrazine compound represented by the formula (2)

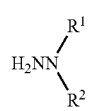

(2)

wherein R¹ and R² are the same as defined above, under acidic conditions in water or an aqueous-organic two layer solvent.

Still further, the present invention provides a method for producing a 5-deoxy-L-arabinose hydrazone represented by the formula (3):

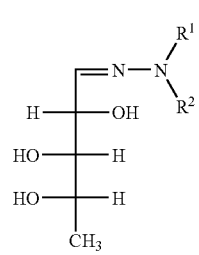

(3)

wherein R¹ and R², which are the same or different from each other, each represents an hydrogen atom, an alkyl group, or aryl group, comprising:

reacting 5-deoxy-L-arabinose with a hydrazine compound represented by the formula (2):

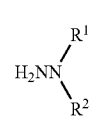

(2)

Wherein R¹ and R² are the same as defined above, under acidic conditions in water or an aqueous-organic two layer solvent.

[Advantages Effects of the Invention]

According to the present invention, L-biopterin can be produced on a large industrial scale by using a reagent which is inexpensive and easy to handle, without requiring a use of any particular equipment or plants. Also, its productivity can be significantly improved due to decreased quantity of reaction solution in process.

[Best Mode for Carrying Out the Invention]

The method for preparing L-biopterin according to the present invention is accomplished in a series of process steps shown below. Hereinafter, these steps of the present method will be described in detail.

[Chemical Formula 7]

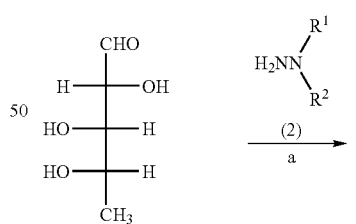

(1)

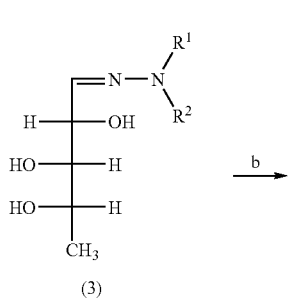

(3)

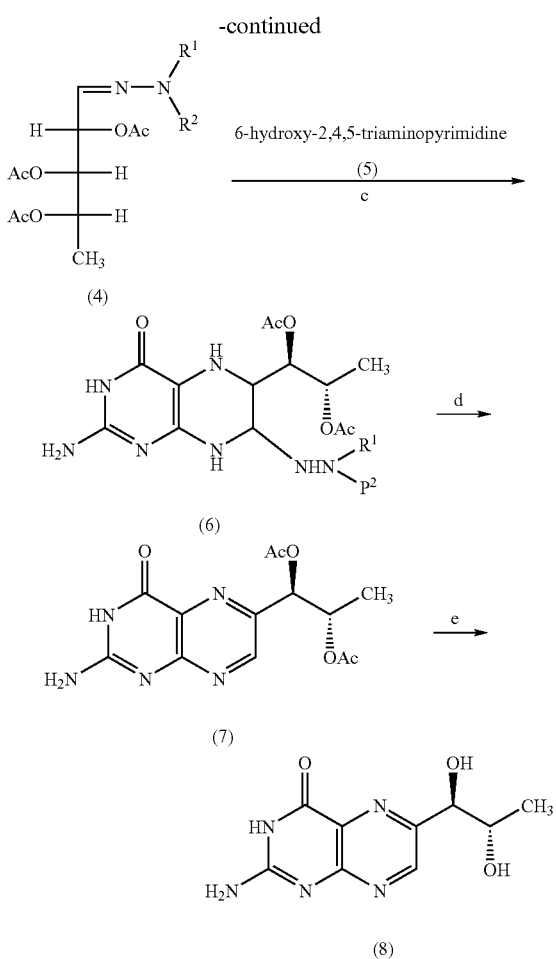

wherein $R^1$ and $R^2$, which are the same or different from each other, each represents a hydrogen atom, an alkyl group, or an aryl group In the series of process steps shown above, 5-deoxy-L-arabinose (1) may be obtained by oxidizing L-rhamnose diethyl mercaptal (REM) to produce 1',1'-diethylsulfonyl-L-rhamnose and subjecting the resultant 1,1'-diethylsulfonyl-L-rhamnose to hydrolysis, for example, in accordance with the method of Max Viscontini, et al. described in the nonpatent literature 1 referred to herein previously. Preferably, the 5-deoxy-L-arabinose (1) thus obtained is fed to the step (a) without isolating it from the reaction solution.

The step (a) subjects 5-deoxy-L-arabinose (1) to reaction with a hydrazine compound (2) to produce a hydrazone compound (3). This step (a) can dispense with the isolation of 5-deoxy-L-arabinose (1) by performing hydrazoniation under acidic conditions in water and separating out hydrazone compound depositing there by filtration. Besides, by adopting an aqueous-organic two layer solvent as a reaction solvent so as to distribute the produced hydrazone compound (3) in its organic solvent, the process can be performed continuously.

The alkyl groups represented by $R^1$ and $R^2$ in the foregoing formula (2) include straight or branched lower alkyl groups having 1 to 7 carbon atoms such as, for example, methyl group and ethyl group, of which the methyl group is preferred. The aryl groups represented by $R^1$ and $R^2$ include those aryl groups having 6 to 14 carbon atoms such as, for example, phenyl group and naphthyl group, among which the phenyl group is preferred. Hydrogen atom or phenyl group is particularly preferred for the groups represented by $R^1$ and $R^2$. The hydrazine compounds preferably used for this process step include, for example, hydrazine, 1,1-dimethyl diazine and phenylhydrazine, among which the phenylhydrazine is particularly preferred.

As the solvent used for this step, water or an aqueous-organic two layer solvent is preferred and particularly the latter solvent is preferred. The organic solvents usable for this purpose include: methyl acetate, ethyl acetate, propyl acetate, and like alkyl acetates; chloroform, methylene chloride, dichloroethane, and like lower alkyl halides; benzene, toluene, and like aromatic hydrocarbons; and diethyl ether, t-butylmethyl ether, isopropyl ether, and like ethers, among which the ethyl acetate is particularly preferred. The mixing ratio (by mass) of water and the organic solvent ranges preferably from about 1:0.5 to about 1:50 and particularly preferably from about 1:0.5 to about 1:1.

The reaction of this step is accomplished under acidic conditions preferably at about pH4.0 to about pH6.5. Acids added to the reaction solvent in this step include organic acids such as acetic acid and inorganic acids such as hydrochloric acid and sulfuric acid.

It is preferred that the reaction be carried out at about 0° C. to 50° C. for about 1 to 3 hours. Upon completing the reaction, the aqueous phase of the reaction solution is extracted with an organic solvent to obtain a hydrazone compound-containing solution, and the latter solution is then fed to the succeeding process step.

The process step (b) shown above acetylates the hydrazone compound (3) fed from the preceding step and produces a triacetoxy-5-deoxy-L-arabinose hydrazone compound represented by the foregoing formula (4). Acetylation can be performed by reacting an acetylating agent in the hydrazone compound-containing solution obtained in the preceding step (a) may be acetylated by reacting it with an acetylating agent in the presence of a catalytic quantity of a dialkylaminopyridine.

The acetylating agents preferably used for the reaction in this step include acetic anhydride and acetyl halide, of which the acetic anhydride is particularly preferred.

The dialkylaminopyridines used as the catalyst in this step include $C_1$-$C_5$ dialkylaminopyridines such as, for example, dimethylaminopyridine (DMAP), and this DMAP is more preferably used.

It is preferred that the reaction be carried out at about 0° C. to 50° C. for about 1 to 24 hours. Upon completing the reaction, a solution containing the triacetylated compound (4) obtained here is fed to the succeeding process step.

Since this step is carried out without concentrating the hydrazone-containing solution obtained in the step (a), it is allowed to prevent the reaction solvent from increasing in volume.

The step (c) is carried out to react the triacetylated compound (4) obtained in the preceding step with the 6-hydroxy-2,4,5-triaminopyrimidine (5) to obtain a biopterin derivative represented by the formula (6) above. The reaction takes place in an aqueous solvent under catalytic influence of a Lewis acid.

As a solvent used for this step, water or water-lower alcohol mixed solvent is preferred and particularly the latter solvent is preferred. Preferable lower alcohols include, for example, methanol, ethanol and isopropanol, among which the methanol is particularly preferred.

The Lewis acid catalysts preferably used for the reaction in this step include aqueous Lewis acid catalysts such as, for example, lithium perchlorate, sodium perchlorate and like alkali metal perchlorates; lithium trifluoromethanesulfonate, sodium trifluoromethanesulfonate and like alkali metal sulfonates; sodium lauryl sulfate and like alkali metal sulfates; and lithium iodate, sodium iodate and like alkali metal halides. Among these, lithium perchlorate and lithium trifluoromethanesulfonate are particularly preferred.

It is preferred that the reaction be carried out at about 20° C. to 80° C. for about 2 to 24 hours.

This step allows the process to maintain yield of the biopterin derivative (6) even with a decreased solvent volume, so that it can be cut down significantly.

The process step (d) oxidizes the biopterin derivative (6) fed from the preceding step and produces a compound represented by the formula (7) above.

The oxidative reaction is carried out preferably adding an oxidizing agent thereto and the oxidizing agents preferably used for this reaction include, for example, oxygen and hydrogen peroxide and like inorganic peracids, and peracetic acid and like organic peracids among which hydrogen peroxide is particularly preferred.

It is preferred that the reaction be carried out at about 0° C. to 50° C. for about 5 to 24 hours. Upon completing the reaction, crystals deposited there are separated out by a conventional solid-liquid separation means (such as a filter, or centrifuge) to obtain a compound represented by the formula (7) shown above.

Besides, this process step causes cleavage of the hydrazine added in the previous step (a).

The process step (e) hydrolyzes the compound (7) obtained in the preceding step to produce L-biopterin represented by the formula (8) shown above.

Preferably, the hydrolysis is carried out in the presence of hydrochloric acid.

It is also preferred that the reaction of this step be carried out at about 40° C. to 60° C. for about 1 to 2 hours. Upon completing the reaction, crystals deposited there after neutralization are separated out by a conventional solid-liquid separation means and dried to obtain L-biopterin represented by the formula (8) above.

In the each process step of the aforementioned processes (a) through (c) the resultant solution containing the product can be used for the next step without purification step.

According to the present invention, since all of the aforementioned process steps can be accomplished totally in single equipment, large scale industrial production of L-biopterin is allowed with improved productivity.

If L-biopterin is prepared in the above-described manner based on the method of the present invention, reaction equipment having a 1,000 c capacity can produce 14 kg or more L-biopterin, as compared with 3 kg output that can be achieved using the same equipment by the prior art method (See nonpatent literature 1: Helv. Chim. Acta 68(6) 1639-43 (1985)).

PREFERRED EXAMPLES

Hereinafter, the present invention will be described in greater detail with reference to the preferred examples thereof, it should be appreciated that the various examples described herein are provided merely for the purpose of illustration and do not constitute any limitations to the present invention.

Example 1

(1) 1',1'-diethylsulfonyl-L-rhamnose 1.2 g of concentrated hydrochloric acid was dissolved in 580 g of acetic acid and then 100 g (0.370 mol) of L-rhamnose diethyl mercaptal was suspended in the resultant solution. Then 200 g (2.06 mol) of a 35% hydrogen peroxide solution was added by dripping to the suspension over 30 minutes, followed by stirring at an ambient temperature of 15° C. over 3 nights. Thereto, was added. An aqueous solution of 4.0 g sodium acetate in 50 ml water. After adding sodium hydrosulfite thereto to deactivate excess hydrogen peroxide, the mixture was subjected to vacuum concentration at an ambient temperature of 40° C. to obtain 1',1'-diethylsulfonyl-L-rhamnose as its crud product.

(2) 5-deoxy-L-arabinose

The 1',1'-diethylsulfonyl-L-rhamnose obtained in the preceding step was dissolved in 500 ml water at an ambient temperature of 40° C. After cooling, the resultant solution was basified with 28% ammonia water. The basified solution was subjected to stirring overnight at an ambient temperature of 20° C. Then crystals deposited there were separated out by filtration and rinsed with water. Subsequently, using ethyl acetate, the water layer was separated and washed twice to obtain an aqueous solution of 5-deoxy-L-arabinose.

(3) 5-deoxy-L-arabinose phenylhydrazone

The aqueous solution of 5-deoxy-L-arabinose obtained in the preceding step was acidified with acetic acid and mixed with 500 me of ethyl acetate added thereto. Then 52.0 g (0.480 mol) of phenylhydrazine was added by dripping to the solution at an ambient temperature of 10° C., followed by stirring for 2 hours at the same ambient temperature. After neutralizing with a 20% aqueous solution of sodium hydroxide, the solution was separated into a water layer and an organic layer, of which the water layer was extracted with 250 ml of ethyl acetate. The organic layer combined with the extract was dried over anhydrous sodium sulfate to obtain an ethyl acetate solution of 5-deoxy-L-arabinose phenylhydrazone.

Example 2

Triacetoxy-5-deoxy-L-arabinose phenylhydrazone

To the ethyl acetate solution of 5-deoxy-L-arabinose phenylhydrazone obtained in the step (3) of the preceding example, 9.0 g (0.074 mol) of 4-dimethylaminopyridine (DMAP) was added and dissolved therein. Then 120.82 g (1.183 mol) of acetic anhydride was added by dripping to the solution at an ambient temperature of 10° C. After stirring overnight at the same ambient temperature, 250 me of water was added to the solution, which was then stirred for 30 minutes. After allowing the solution to stand, it was separated into a water layer and an organic layer, and a 20% aqueous solution of sodium hydroxide was added to the organic layer up to its neutralization. Then after allowing the solution to stand, its organic layer was separated out and dried over anhydrous sodium sulfate. When the thus treated ethyl acetate solution was subjected to vacuum concentration, an ethyl acetate solution of triacetoxy-5-deoxy-L-arabinose phenylhydrazone was obtained.

Example 3

Tetrahydropterin Derivative

To the ethyl acetate solution of triacetoxy-5-deoxy-L-arabinose phenylhydrazone obtained in the preceding example, were added 500 me of methanol, 41.74 g (0.296 mol) of 6-hydroxy-2,4,5-triaminopyrimidine and 300 ml of water in the cited order. Further, 23.73 g (0.140 mol) of lithium perchlorate trihydrate dissolved in 200 ml water was added thereto and the resultant solution was stirred at 50° C. for 6 hours to obtain an aqueous solution of a tetrahydropterin derivative.

Example 4

1,2'-O-diacetyl-L-biopterin

A 35% hydrogen peroxide solution (1.405 mol) was added by dripping to the aqueous tetrahydropterin derivative solution obtained in the preceding example and the resultant mixture was stirred at 20° C. for 8 hours. Crystals deposited there were separated out by filtration and rinsed with water and methanol to obtain 1',2'-O-diacetyl-L-biopterin.

Example 5

L-biopterin

The 1',2'-O-diacetyl-L-biopterin obtained in the preceding example was suspended in 3 mol/l hydrochloric acid and the resultant suspension was stirred at 50° C. for 2 hours. After decoloring with activated charcoal, the reaction solution was neutralized with 28% ammonia water. Subsequently, crystals deposited there were separated out by filtration and dried to obtain 23.13 g of L-biopterin.

What is claimed is:

1. A method for producing a compound represented by formula (6):

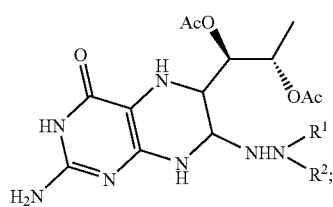

(6)

wherein $R^1$ and $R^2$, which are the same or different from each other, each represents a hydrogen atom, an alkyl group, or an aryl group, comprising:

reacting a triacetoxy-5-deoxy-L-arabinose phenylhydrazone of formula (4):

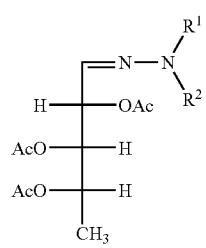

(4)

wherein $R^1$ and $R^2$ which are the same or different from each other, each represents a hydrogen atom, an alkyl group, or an aryl group;

with 6-hydroxy-2,4,5-triaminopyrimidine (5) under catalytic influence of a Lewis acid in an aqueous solvent.

2. The method according to claim 1, wherein said aqueous solvent is water or a water-lower alcohol mixed solvent.

3. The method according to claim 1, wherein said Lewis acid is an aqueous Lewis acid catalyst.

4. The method according to claim 1, wherein said Lewis acid is one selected from the group consisting of alkali metal perchlorates, alkali metal sulfonates, alkali metal sulfates and alkali metal halides.

5. A method for producing 1',2'-O-diacetyl-L-biopterin, comprising oxidizing the compound represented by formula (6) obtainable by a method according to claim 1.

6. The method according to claim 5, wherein said oxidizing step is carried out using hydrogen peroxide.

7. A method for producing L-biopterin, comprising hydrolyzing the 1',2'-O-diacetyl-L-biopterin obtainable by a method according to claim 5.

8. The method according to claim 7, wherein said hydrolyzing step is carried out in the presence of hydrochloric acid.

9. The method according to claim 1, wherein said compound represented by formula (4) is obtained by:

reacting a compound represented by the formula (3) with an acetylating agent in the presence of a catalytic quantity of dialkylaminopyridine; wherein formula (3) is:

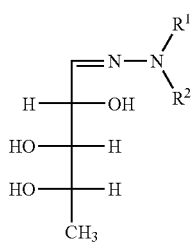

(3)

wherein $R^1$ and $R^2$, which are the same or different from each other, each represents a hydrogen atom, an alkyl group, or an aryl group.

10. The method according to claim 9, wherein said acetylating agent is one selected from the group consisting of acetic anhydride and acetyl halides.

11. The method according to claim 9, wherein said compound represented by formula (3) is obtained by:

reacting 5-deoxy-L-arabinose with a hydrazine compound represented by formula (2) under acidic conditions in water or in a water-organic two-layer solvent;

wherein the compound of formula 2 is:

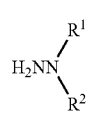

(2)

wherein $R^1$ and $R^2$, which are the same or different from each other, each represents an hydrogen atom, an alkyl group, or an aryl group.

12. The method according to claim 11, wherein said organic solvent is one selected from the group consisting of alkyl acetates, lower alkyl halides, aromatic hydrocarbons and ethers.

13. The method of claim 5, wherein the oxidizing step is carried out without using iodine.

14. The method of claim 7 which produces at least 14 kg of biopterin per 1,000 liters of reaction equipment capacity.

* * * * *